(12) United States Patent
Kojima et al.

(10) Patent No.: US 9,289,367 B2
(45) Date of Patent: Mar. 22, 2016

(54) COSMETIC BASE COMPRISING COLLAGEN-MODIFIED LIPOSOME AND SKIN COSMETIC CONTAINING THE SAME

(75) Inventors: Tsuyoshi Kojima, Nara (JP); Shinichi Kojima, Nara (JP); Hiroyuki Yoshikawa, Shiga (JP); Tomomi Kazumori, Hyogo (JP); Teruhisa Kaneko, Tokyo (JP); Chihiro Kaise, Tokyo (JP)

(73) Assignee: Faith, Inc., Osaka (JP)

( * ) Notice: Subject to any disclaimer, the term of this patent is extended or adjusted under 35 U.S.C. 154(b) by 10 days.

(21) Appl. No.: 12/659,653

(22) Filed: Mar. 16, 2010

(65) Prior Publication Data

US 2011/0081402 A1    Apr. 7, 2011

(30) Foreign Application Priority Data

Oct. 2, 2009    (JP) ................. 2009-230825

(51) Int. Cl.
| | |
|---|---|
| *A61K 9/127* | (2006.01) |
| *A61Q 19/00* | (2006.01) |
| *A61K 8/65* | (2006.01) |
| *A61K 8/14* | (2006.01) |

(52) U.S. Cl.
CPC ... *A61K 8/65* (2013.01); *A61K 8/14* (2013.01); *A61Q 19/00* (2013.01)

(58) Field of Classification Search
CPC ............ A61K 8/14; A61K 8/65; A61Q 19/00
USPC ..................... 424/70.4, 450; 514/17.2, 18.8
See application file for complete search history.

(56) References Cited

U.S. PATENT DOCUMENTS

| 5,244,672 A | 9/1993 | Huc et al. |
| 5,846,561 A | 12/1998 | Margalit |
| 6,146,650 A | 11/2000 | Redlinger |

FOREIGN PATENT DOCUMENTS

| GB | 2 226 002 | 6/1990 |
| KR | 2009-0037723 | 4/2009 |

OTHER PUBLICATIONS

Yerushalmi et al. (Biochim Biophys Acta. Jan. 3, 1994;1189(1):13-20).*
Yerushalmi et al. (Arch Biochem Biophys. Sep. 1994; 313(2): 267-73), abstract only.*
M. Takada et al., "Increased Lung Uptake of Liposomes Coated with Polysaccharides", Biochimica et Biophysica Acta, vol. 802, pp. 237-244, 1984.
J. Moellerfeld et al., "Improved Stability of Black Lipid Membranes by Coating with Polysaccharide Derivatives Bearing Hydrophobic Anchor Groups", Biochimica et Biophysica Acta, vol. 857, pp. 265-270, 1986.
J. Sunamoto et al., "Naturally Occurring Polysaccharide Derivatives Which Behave as an Artificial Cell Wall on an Artificial Cell Liposome", Macromolecules, vol. 25, pp. 5665-5670, 1992.
Extended European Search Report dated Apr. 11, 2011 in European Application No. 10157504.1.
A. M. Del Pozo et al., "Interaction of Type I Collagen Fibrils with Phospholipid Vesicles", Matrix, vol. 9, pp. 405-410, Jan. 1, 1989.
I. Elron-Gross et al., "Cyclooxygenase Inhibition by Diclofenac Formulated in Bioadhesive Carriers", Biochimica et Biophysica Acta, vol. 1778, No. 4, pp. 931-936, Apr. 4, 2008.
N. Yerushalmi et al., "Bioadhesive, Collagen-Modified Liposomes: Molecular and Cellular Level Studies on the Kinetics of Drug Release and on Binding to Cell Monolayers", Biochimica et Biophysica Acta, vol. 1189, No. 1, pp. 13-20, 1994.
Database WPI, Week 200566, Thomson Scientific, London, GB; AN 2005-642467, XP002629770 & JP 2005-179313, Jul. 7, 2005, Abstract.
M. Pajean et al., "Effect of Collagen on Liposome Permeability", International Journal of Pharmaceutics, vol. 91, No. 2-3, pp. 209-216, Apr. 26, 1993.
D. Nelson et al., Lehninger Principles of Biochemistry, 3$^{rd}$ Edition, pp. 173-174, 2000.
Yokoyama et al., "Analysis of Hydroxyproline Found in Collagen by Reversed-Phase High-Performance Liquid Chromatography", Annals of Gunma University School of Health Sciences, vol. 24, No. 11, 2003, pp. 111-116 (with English abstract).

* cited by examiner

*Primary Examiner* — Janet Epps-Smith
(74) *Attorney, Agent, or Firm* — Wenderoth, Lind & Ponack, L.L.P.

(57) ABSTRACT

The affinity of collagen for the skin and its persistence on the skin are improved without destroying the triple helical structure inherent in collagen to thereby improve its ability to retain the moisture of the skin and increase the amount of bound water when such collagen is used as a skin cosmetic. The collagen can thereby exert its moisture retention effect more effectively. A cosmetic base includes an aqueous solution of a liposome that is surface-modified with water-soluble collagen having a triple helical structure.

7 Claims, No Drawings

COSMETIC BASE COMPRISING COLLAGEN-MODIFIED LIPOSOME AND SKIN COSMETIC CONTAINING THE SAME

BACKGROUND OF THE INVENTION

1. Field of the Invention

The present invention relates to a cosmetic base comprising a collagen-modified liposome and a skin cosmetic containing the cosmetic base.

2. Description of the Related Art

Collagen is a family of fibrous proteins that constitute our body and is the main component of the dermis of skin tissue. Collagen in normal skin serves as the support structure of the skin and properly supports the epidermis, making the skin elastic and resilient. Collagen has a triple helical structure, and this structural shape provides a very high moisture retention ability and allows a large amount of bound water.

Various skin cosmetics, supplements, and other products have been developed with the expectation that the high moisture retention ability of collagen will provide a high moisturizing effect. However, the average molecular weight of collagen is very large (approximately 200 thousand to approximately 400 thousand). Therefore, to improve solubility in preparations and permeability into the skin, gelatin produced by heat treatment of collagen to improve solubility or low molecular weight gelatin (so called hydrolyzed collagen) produced by chemically and/or enzymatically cutting such gelatin is used.

PRIOR ART REFERENCES

[Non-Patent Document 1] Takada, M., Yuzuriha, T., Katayama, K., Iwamoto, and K., Sunamoto, J., Biochim. Biophys. Acta, 802, 237 (1984).

[Non-Patent Document 2] Sunamoto, J., Iwamoto, K., Takada, M., Yuzuriha, T., and Katayama, K., in Polymers in Medicine; Chiellini, E., Giusti, P. A., Eds. Plenum Publishing Co. New York, 1984, p. 157.

[Non-Patent Document 3] Moellerfeld, J., Prass, W., Ringsdorf, H., Hamazaki, H., Sunamoto, J., J. Biochim. Biophys. Acta, 857, 265 (1986).

[Non-Patent Document 4] Sunamoto, J., Sato, T., Taguchi, T., Hamazaki, H., Macromolecules, 25, 5567 (1992).

These papers describe that liposomes coated with hydrophobic group-modified polysaccharides can be prepared by chemically bonding hydrophobic long-chain alkyl groups or hydrophobic cholesterol to polysaccharides such as pullulan and mixing the resultant hydrophobic group-modified polysaccharides with liposomes. In the above process, the hydrophobic groups are spontaneously attached to the liposome membranes. With the above technique, the contents of the liposomes are prevented from leaking, so that the liposomes are stabilized. In addition, the coatings allow the liposomes to be stabilized in blood. However, the technique described in these papers is not applicable to collagen. This is because, since a heating step must be used to introduce hydrophobic groups to collagen molecules, their triple helical structure is destroyed. Moreover, the coating method and the object of the coating are different from those of the invention. Therefore, these papers are considered as prior art references in terms of coating a liposome with a polymer material but are obviously different from the present invention in their coating techniques and objects.

SUMMARY OF THE INVENTION

It is an object of the present invention to improve the affinity of collagen for the skin and its persistence in the skin without destroying the triple helical structure inherent in collagen to thereby improve its ability to retain the moisture of the skin and increase the amount of bound water when such collagen is used as a skin cosmetic. The collagen can thereby exert its moisture retention effect more effectively.

The present inventors have made extensive studies and found that the above object can be achieved by using a collagen-modified liposome prepared by adsorbing water-soluble collagen retaining its triple helical structure onto the surface of a liposome having a bilayer structure similar to the structure of stratum corneum intercellular lipid. Thus, the invention has been completed.

Accordingly, the present invention relates to the following aspects:

(1) A cosmetic base comprising an aqueous solution of a liposome surface-modified with water-soluble collagen having a triple helical structure.

(2) The cosmetic base according to (1), further comprising hyaluronic acid and/or hydrolyzed elastin.

(3) The cosmetic base according to (1) or (2), wherein the water-soluble collagen having the triple helical structure is atelocollagen.

(4) The cosmetic base according to any one of (1) to (3), wherein the cosmetic base is freeze-dried.

(5) A skin cosmetic comprising the cosmetic base according to any one of (1) to (3).

(6) The skin cosmetic according to (5), wherein the skin cosmetic is freeze-dried.

The collagen-modified liposome in the present invention is not subjected to chemical or other treatment for improving the solubility and dispersibility in water and is prepared by adsorbing water-soluble collagen retaining its original triple helical structure onto a liposome. The use of the collagen having a high moisture retention ability can provide cosmetics having a high moisture retention effect on the skin.

Generally, when water-soluble collagen coexists with hyaluronic acid, a complex is formed due to their charged states. In such a case, the solution becomes non-uniform, and their original water retention functions are not fully exerted. However, according to the present invention, water-soluble collagen is adsorbed onto a liposome having a controlled surface charge, so that the structure of the water-soluble collagen can be stabilized. Therefore, a uniform and stable composition can be obtained without the formation of the above complex even under the coexistence with hyaluronic acid or hydrolyzed elastin.

To maintain the triple helical structure of the collagen included in formulations containing free water such as aqueous solutions, gels, and emulsions, the formulations are manufactured and stored at a temperature equal to or less than the denaturation temperature of the collagen (20 to 30° C. for fishes, 36 to 38° C. for mammals) to maintain the triple helical structure. When such a formulation is freeze-dried, the amount of the free water can be reduced to 0%, and the triple helical structure can thereby be maintained at a temperature equal to or higher than the denaturation temperature. Before the use of the freeze-dried composition, an aqueous solution is added thereto to disperse the freeze-dried composition, and the dispersion is applied to the skin. Then the dispersion is stored and maintained at a temperature equal to or less than the denaturation temperature. Even in the formulation of such a preparation-before-use type, the triple helical structure of the collagen can be stabilized. When free water is present, the triple helical structure of collagen is destroyed at the denaturation temperature or higher, and gelatin is formed. However, even when water is present, the triple helical structure is not destroyed at the denaturation temperature or higher so long as the water is bound water.

DETAILED DESCRIPTION OF THE PREFERRED EMBODIMENT

A collagen-modified liposome used in a cosmetic base of the present invention is prepared by subjecting a liposome having a controlled surface charge to surface treatment, more specifically by adsorbing water-soluble collagen onto the liposome.

To provide a positive surface charge to a liposome, positively charged phosphatidylethanolamine, a positively charged dialkyl ether ammonium salt, or the like is added to phosphatidylcholine (having a neutral surface charge), which is the main component of the liposome membrane. A positively charged liposome is thereby obtained.

To provide a negative surface charge to a liposome, negatively charged dicetyl phosphate, negatively charged phosphatidylinositol, negatively charged phosphatidylglycerol, negatively charged phosphatidic acid, or the like is added to phosphatidylcholine (having a neutral surface charge), which is the main component of the liposome membrane. A negatively charged liposome is thereby obtained.

To control the charge of the water-soluble collagen to be adsorbed onto the surface of the liposome, enzyme treatment is used to provide positively charged collagen, and alkali treatment is used to provide negatively charged collagen.

The average molecular weight of the liposome may be appropriately selected between approximately 10,000 to approximately 3,000,000.

The water-soluble collagen may be adsorbed onto the surface of the liposome at a molar ratio of liposome:collagen=1:0.01 to 1:100 and preferably 1:0.1 to 1:10.

The water-soluble collagen used in the present invention is not subjected to chemical or other treatment for improving solubility and dispersibility in water and retains the triple helical structure. The molecular weight of the water-soluble collagen is preferably approximately 200 thousand to approximately 400 thousand. Atelocollagen obtained by removing telopeptides at both ends of collagen molecules is more preferred to eliminate a telopeptide-induced allergic reaction, which, however, occurs only rarely.

Generally, to avoid complications of manufacturing and storage and to improve solubility in water, heat-treated gelatin or low-molecular collagen prepared by cutting untreated collagen molecules using chemical or enzyme treatment to reduce their original molecular weight are used in most cases. However, the water-soluble collagen used in the present invention is untreated collagen retaining its original triple helical structure and therefore has a high moisture retention ability.

The liposome used in the present invention is a closed vesicle composed of a monolayer or multilayers of phospholipids bilayer. This liposome is obtained by mixing the phospholipid with water and has a high affinity for cells. Examples of the base material for forming the liposome membrane include: natural and synthetic phospholipids such as phosphatidylcholine, phosphatidylethanolamine, phosphatidylinositol, phosphatidylserine, phosphatidylglycerol, phosphatidic acid, lysophosphatidylcholine, sphingomyelin, egg-yolk lecithin, soybean lecithin, and hydrogenated products thereof; cholesterols such as cholesterol and alkyl esters thereof; phytosterols and alkyl esters thereof; glyceroglycolipids; acylglucosides such as cetylgalactoside; dicetyl phosphate; dialkyl-type synthetic surfactants; N-acylsphingosine and a sulfate thereof; N-acyl glycosphingolipid; N-higher acyl glutathiones; and mixtures of two or more thereof. If necessary, a polyalcohol, a higher alcohol, a higher fatty acid, or the like may be added to stabilize the liposome or to improve the phase transition temperature thereof.

The liposome may contain a hydrophilic medicinal component and/or a lipophilic medicinal component. Examples of the hydrophilic and lipophilic medicinal components include antioxidants, antibacterial agents, anti-inflammatory agents, blood circulation promoters, whitening agents, skin conditioners, anti-aging agents, moisturizers, hormones, vitamins, coloring agents, and proteins.

Examples of the method of manufacturing the liposome include an ultrasonic method, ethanol injection method, cholic acid removal method, reverse phase evaporation method, extruder method, and microfluidizer method.

When hyaluronic acid and/or hydrolyzed elastin that have a high moisture retention effect is also present, a high-functionality moisturizing cosmetic having a high moisture retention ability can be produced, and this allows the control of wrinkles caused by dry skin and the turn over of the skin.

Elastin, as well as collagen, is an important protein found in connective tissues such as nuchal ligament, blood vessels, and skin but is almost insoluble in water. In the present invention, the hydrolyzed elastin is obtained by subjecting nuchal ligament or the like to enzyme treatment or oxalic acid treatment to improve the solubility in water.

In the present invention, a cosmetic base containing the collagen-modified liposome described above or a mixture of the collagen-modified liposome, hyaluronic acid and/or hydrolyzed elastin may be used for a skin cosmetic.

No particular limitation is imposed on the skin cosmetic of the present invention. Examples of the skin cosmetic include: face care cosmetics such as essences, milky lotions, creams, skin lotions, packs, facial cleansers, massage creams; make-up cosmetics including liquid foundations, emulsified foundations, and powder foundations; and body cosmetics.

In the skin cosmetic of the present invention, the reference amount of the collagen-modified liposome in the skin cosmetic is 0.001 to 10 wt % and preferably 0.01 to 5 wt %.

In the skin cosmetic of the present invention, the ratio of the amount of the collagen-modified liposome and the total amount of hyaluronic acid and/or hydrolyzed elastin may be adjusted freely. However, the ratio of the total amount of hyaluronic acid and/or hydrolyzed elastin to the amount of the skin cosmetic is preferably 0.001 to 10 wt % and more preferably 0.005 to 1 wt %. When the total amount exceeds the above range, the dispersibility in water deteriorates. This can adversely affect the stability (for example, separation, discoloration, or change in odor) and the sensory properties of the skin cosmetic.

In addition to the essential ingredients described above, any of components generally added to cosmetics may be appropriately selected and added so long as the effects of the present invention are not impaired. Examples of such components include fats and oils, hydrocarbons, waxes, fatty acids, synthetic esters, alcohols, powders, surfactants, thickeners, polymer compounds, gelling agents, UV absorbers, UV dispersing agents, antioxidants, coloring agents, pigments, preservatives, perfumes, medications, and water.

Examples of the fats and oils include jojoba oil, castor oil, olive oil, soybean oil, coconut oil, palm oil, cocoa butter, mink oil, and turtle oil.

Examples of the hydrocarbons include liquid paraffin, vaseline, microcrystalline wax, and squalane.

Examples of the waxes include beeswax, lanoline, carnauba wax, and candelilla wax.

Examples of the fatty acids include myristic acid, palmitic acid, stearic acid, oleic acid, isostearic acid, and lauric acid.

Examples of the synthetic esters include isopropyl myristate, isopropyl palmitate, butyl oleate, myristyl myristate, octyldodecyl myristate, propylene glycol monostearate, myristyl lactate, and isostearyl malate.

The ratio of the total amount of the fats and oils, hydrocarbons, waxes, fatty acids, and synthetic esters to the amount of the skin cosmetic is generally 0 to 30 w/w %.

Examples of the alcohols include ethanol, 1,3-butylene glycol, propylene glycol, lauryl alcohol, cetanol, stearyl alcohol, and oleyl alcohol. The alcohols are added to the skin cosmetic at a ratio of 0 to 25 w/w %.

Examples of the surfactants include polyglycerin fatty acid esters, sorbitan fatty acid esters, polyoxyethylene fatty acid esters, polyoxyethylene sorbitan fatty acid esters, polyoxyethylene alkyl ethers, coconut oil fatty acid monoethanolamides, polyoxyethylene hydrogenated castor oil, sodium lauryl sulfate, polyoxyethylene glyceryl pyroglutamate isostearate, sodium alkylbenzene sulfonates, polyoxyethylene stearyl ethers, dialkyl sulfosuccinates, cetylpyridinium bromide, n-octadecyltrimethylammonium chloride, monoalkyl phosphates, N-acylsulfamate, N-acylglutamine, sucrose fatty acid esters, polyoxyethylene sorbitan monostearate, polyoxyethylene lauryl ether sodium sulfate, polyoxyethylene hydrogenated lanolin, and sugar esters. Generally, the surfactants are added to the skin cosmetic at a ratio of 0 to 10 w/w %.

Examples of the thickeners include carboxyvinyl polymers, methylpolysiloxane, dextran, carboxymethyl cellulose, carrageenan, and hydroxypropyl methyl cellulose. Generally, the thickeners are added to the skin cosmetic at a ratio of 0 to 5 w/w %.

Examples of the moisturizers include glycerine, propylene glycol, 1,3-butylene glycol, pyroglutamic acid, acetyl glutamic acid, and procyanidin. Generally, the moisturizers are added to the skin cosmetic at a ratio of 0 to 25%.

Examples of the preservatives include: benzoic acid, salicylic acid, dehydroacetic acid, and salts thereof; phenols such as p-oxybenzoic acid ester; triclosan; and halocarbon. Generally, the preservatives are added to the skin cosmetic at a ratio of 0 to 0.3 w/w %.

Any of the perfumes generally used in cosmetics may be used.

Examples of the pigments include iron oxide, titanium dioxide, zinc oxide, kaolin, and talc. Generally, the pigments are added to the skin cosmetic at a ratio of 0 to 5 w/w %.

Examples of the medications include wheat germ oils, vitamin A, vitamin B2, vitamin E, magnesium ascorbic acid-2-phosphate, sodium ascorbic acid-2-phosphate, D-pantothenyl alcohol, dipotassium glycyrrhizinate, glutathione, UV absorbers, chelating agents, plant extracts, and microbial metabolites/extracts. Generally, the medications are added to the skin cosmetic at a ratio of 0 to 5 w/w %.

Examples of the water include tap water, mineral water, salt water, seawater, deep sea water, ultrapure water, water from polar ice, mineral-containing water, and purified water. The water is added in any ratio.

In the present invention, the deep sea water is low-temperature and clean proper water containing various nutritive salts and obtained from a layer of sedimented surface sea water. The deep sea water is taken from a sea area between 1,000 and 4,000 m and preferably 2,000 and 3,000 m at a depth of 250 to 500 m and preferably 300 to 400 m.

Since the deep sea water contains various minerals, it is excellent in moisture retention ability and permeability. Therefore, the deep sea water may facilitate the penetration of the active ingredients contained in the cosmetic into the skin.

The skin cosmetic of the present invention may take any form such as a solubilized system, an emulsion system or a dispersion system.

In the present invention, the cosmetic base and the skin cosmetic described above may be freeze-dried to store them at a temperature equal to or higher than the denaturation temperature of the collagen. In the freeze dry process, the phase change occurs on the solid-liquid equilibrium line at a pressure equal to or less than the pressure at the triple point, and moisture is directly vaporized from its solid phase (ice) by sublimation, so that the moisture is removed, i.e., dried. The dehydration-drying process by sublimation is referred to vacuum freeze drying. With this process, active ingredients that are easily denatured by temperature in the presence of water can be stabilized. In the present invention, an aqueous solution of the collagen-modified liposome is freeze-dried to prepare a solid preparation from which moisture has been removed. When the preparation is used, an aqueous solution is added thereto and shaken to obtain an uniform dispersion of the collagen-modified liposome. After applied to a certain area of the face, the dispersion is stored at 20° C. or less. In this manner, the collagen having the triple helical structure can be stably supplied, and the collagen can be absorbed into the stratum corneum of the skin as the liposome penetrates into the skin.

Examples and Test Examples of the present invention are shown below.

However, the present invention is not limited to the Examples.

Example 1

Aqueous Solution of Liposome Modified with Water-Soluble Collagen

An aqueous solution of a liposome containing egg-yolk lecithin (0.9 wt %) was prepared by the extruder method (M. J. Hope, M. B. Bally, G. Webb, and P. R. Cullis, Biochim. Biophys. Acta, vol. 812, 55 (1985)). The prepared liposome membrane included egg-yolk lecithin:cholesterol:dicetyl phosphate=4:4:2 (in molar ratio), had a pH of 7.0, and was negatively charged. The average molecular weight of the liposome was approximately 500 thousand to approximately one million. The prepared aqueous solution of the liposome and a 0.5 wt % pH-neutral aqueous solution of positively charged atelocollagen were mixed at 18° C. at a ratio of 1:5. More specifically, the aqueous solution of atelocollagen having a molecular weight of approximately 300 thousand was added dropwise to the aqueous solution of the liposome under stirring. The mixture was stirred for one hour using a dispersing apparatus to obtain an aqueous solution of the liposome modified with the water-soluble collagen. The obtained aqueous solution was stored at 5° C.

Example 2

Aqueous Solution of Liposome Modified with Water-Soluble Collagen

An aqueous solution of a liposome containing egg-yolk lecithin (1.2 wt %) was prepared by the extruder method (M.

J. Hope, M. B. Bally, G. Webb, and P. R. Cullis, Biochim. Biophys. Acta, vol. 812, 55 (1985)). The prepared liposome membrane included egg-yolk lecithin:cholesterol:phosphatidylethanolamine=4:4:2 (in molar ratio), had a pH of 7.0, and was positively charged. The average molecular weight of the liposome was approximately 500 thousand to approximately one million. The prepared aqueous solution of the liposome and a 0.5 wt % pH-neutral aqueous solution of negatively charged atelocollagen having a molecular weight of approximately 300 thousand were mixed at 18° C. at a ratio of 2:5. More specifically, the aqueous solution of atelocollagen was added dropwise to the aqueous solution of the liposome under stirring. The mixture was stirred for one hour using a dispersing apparatus to obtain an aqueous solution of the liposome modified with the water-soluble collagen. The obtained aqueous solution was stored at 5° C.

Example 3

Freeze-Dried Preparation Comprising Liposome Surface-Modified with Water-Soluble Collagen, Hyaluronic Acid, and Hydrolyzed Elastin 10 Parts by weight of a 0.5 wt % aqueous solution of sodium hyaluronate was added dropwise at 17° C. to 40 parts by weight of the aqueous solution of the liposome surface-modified with the water-soluble collagen obtained in Example 1. Next, 50 parts by weight of a 0.1 wt % aqueous solution of hydrolyzed elastin was added dropwise to the mixture, and the resultant mixture was stirred at the same temperature of 17° C. for 30 minutes. 10 Parts by weight of mannitol was dissolved in 90 parts by weight of the prepared solution under stirring. The resultant solution was freeze-dried to give a freeze-dried composition. Water was added to the composition to give an aqueous solution comprising the liposome surface-modified with the water-soluble collagen, hyaluronic acid, and hydrolyzed elastin. The precipitate of a complex of collagen and sodium hyaluronate, which is generally observed, was not found.

The stability of the triple helical structure of the water-soluble collagen in the freeze-dried composition was observed after storing for one month at 45° C. The stability of the triple helical structure was determined using SDS-polyacrylic amide gel electrophoresis. In addition to this, the stability of the triple helical structure was determined also by comparing the viscosity of a sample prepared using the freeze-dried composition with the viscosity of the same sample stored at a temperature equal to or lower than the denaturation temperature (when the triple helical structure is destroyed, the viscosity decreases).

TABLE 1

|  | 3 Hours after | 14 Hours after | 30 Days after |
| --- | --- | --- | --- |
| Aqueous solution of Example 1 | X | X | X |
| Freeze dried composition of Example 3 | O | O | O |

Cross: Triple helical structure not observed/Circle: Triple helical structure observed As can be seen from the results shown in Table 1, the stability of the freeze dried composition was obviously better and satisfactory as a product.

Example 4

Essence Containing Liposome Surface-Modified with Water-Soluble Collagen

A liposome essence comprising egg-yolk lecithin (1.5 wt %), cholesterol (0.3 wt %), dicetyl phosphate (0.2 wt %), oleic acid (0.5 wt %), stearyl alcohol (0.3 wt %), glycerin stearate (2.0 wt %), arginine (0.7 wt %), 1,3-butylene glycol (5 wt %), dipropylene glycol (2 wt %), glycerin (3 wt %), corn oil (1.5 wt %), avocado oil (1 wt %), polyglyceryl-5 oleate (0.5 wt %), and purified water (sufficient to make 100 wt %) was prepared using an LLC method (T. Kaneko and H. Sagitani, Colloids & Surfaces, vol. 69, 125 (1992)). 10 Parts by weight of a 0.5 wt % aqueous solution of positively charged atelocollagen was added dropwise to 80 parts by weight of the essence at 15° C., and the mixture was stirred for 10 minutes. Then 10 parts by weight of 0.5% sodium hyaluronate was added dropwise to the mixtures under stirring, and the resultant mixture was stirred for 10 minutes to give the target essence. The essence was observed under a microscope, and a complex of collagen and sodium hyaluronate, which is generally observed, was not found.

Test Example 1

Absorption Ability Test of Collagen into Stratum Corneum

The absorbability of collagen into the stratum corneum of human skin was tested using the aqueous solution of the liposome surface-modified with the water-soluble collagen that was obtained in Example 1 and an aqueous solution of collagen having the same concentration as that of the above aqueous solution (0.083 wt %). The number of subjects n was 8. Each sample was applied to the inner brachium treated with an acetone-ether (1/1) solution, and the applied area was covered with a patch. Measurement samples were collected 15 hours after application.

Method of quantifying the amount of collagen absorbed into the stratum corneum: 15 Hours after application, the applied sample remaining on the skin was wiped off using purified water and ethanol, and the stratum corneum was collected using a tape stripping method (second to fifth layers, sixth to tenth layers, and eleventh to fifteenth layers were collected and used as the measurement samples). The first one of the collected tapes was eliminated, and the second and later tapes were used as the measurement samples. Water soluble components in the collected tapes were extracted, and the amounts of hydroxyproline in the water soluble components were measured. The absorption amounts in terms of collagen were computed (the amount of hydroxyproline in an unapplied control area was used as blank).

TABLE 2

|  | Second to fifth layers | Sixth to tenth layers | Eleventh to fifteenth layers |
| --- | --- | --- | --- |
| Collagen-modified liposome | 0.0200% | 0.0100% | 0.0024% |
| Aqueous solution of collagen | 0.0033% | 0.0002% | Not detectable |

As can be seen from the results shown in Table 2, almost no collagen in the form of an aqueous solution was absorbed into the stratum corneum. However, the absorption into the stratum corneum was facilitated by adsorbing collagen onto the liposome.

Test Example 2

Moisture Retention Ability Test of Aqueous Solution of Example 2

The experimental conditions are as follows.
(Experimental Conditions)

The inner brachium was treated with an SDS solution to form rough dry skin. Two days after the treatment, the measurement was started. More specifically, the aqueous solution of Example 2 was applied once in the morning and once at night.

The number of subjects was 6, and the subjects were allowed to stand in a room at a controlled temperature of 20±1° C. and a controlled humidity of 40±5 RH % for 30 minutes. Then the amounts of water in their stratum corneum were measured. The measurement results are shown in Table 3. Measurement apparatus: Skin Surface Hygrometer [SKICON-200] (the amount of water in the stratum corneum was measured in the unit of μS)

TABLE 3

|  | At start of test | 2 Weeks after | 4 Weeks after |
|---|---|---|---|
| Control | 11 | 12.7 | 14.9 |
| Aqueous solution of Example 2 | 10.3 | 18.6 | 22.3 |

Control means uncoated areas

As can be seen from Table 3, the dry skin improving effect of the aqueous solution of Example 2 was higher than that of the control.

Test Example 3

Skin Resiliency Recovery Effect of Essence of Example 4

The experimental conditions are as follows.
(Experimental Conditions)

The inner brachium was treated with acetone-ether (1/1) (treated twice at a 3 day interval) to form rough dry skin. On the next day, the measurement was started. More specifically, the essence of Example 4 was applied once in the morning and once at night. The number of subjects was 8, and the subjects were allowed to stand in a room at a controlled temperature of 20±1° C. and a controlled humidity of 40±5 RH % for 60 minutes or more. Then the viscosities of their skin were measured. The results are shown in Table 4. Measurement apparatus: Dermal Torque Meter (product of Dia-Stron). The closer DTM value (Ur/Ue) to 1, the higher the viscosity of the skin, and the better the recovery.

TABLE 4

|  | At start of test | 3 Weeks after | 6 Weeks after |
|---|---|---|---|
| Control | 0.183 | 0.196 | 0.230 |
| Essence of Example 4 | 0.179 | 0.233 | 0.268 |

Control means uncoated areas

As can be seen from Table 4, the essence of Example 4 can recover the resiliency faster than the control with a significant difference.

In the cosmetic base of the present invention, the structure of water-soluble collagen can be retained. Even in the presence of hyaluronic acid and hydrolyzed elastin, a complex is not formed. Therefore, a preferable skin cosmetic can be provided.

What is claimed is:

1. A method for producing a cosmetic base which promotes permeation of a collagen into a stratum corneum of skin and which, in an environment at a temperature of 20° C. or less comprises the following steps:
   (1) preparing an aqueous solution of a liposome controlled to have a positive or negative surface charge by a charge of a film-forming material;
   (2) dropping into the aqueous solution of (1) a water-soluble collagen which is controlled to have a charge opposite to the charge of the liposome, while retaining a triple helical structure, and which is to be adsorbed on the surface of the liposome, to form a mixture; and
   (3) stirring the mixture of (2) for the water-soluble collagen to be adsorbed on the surface of the liposome by electrostatic force.

2. The method for producing the cosmetic base according to claim 1, wherein the water-soluble collagen is treated with an enzyme to be controlled to have a positive charge.

3. The method for producing the cosmetic base according to claim 1, wherein the water-soluble collagen is treated with an alkali to be controlled to have a negative charge.

4. A skin cosmetic containing an aqueous solution of a liposome modified with a collagen, wherein an aqueous solution containing atelocollagen at 0.5 wt % being a water-soluble collagen controlled to have a positive surface by enzyme treatment, while having a triple helical structure, is dropped into an aqueous solution of a liposome with a liposome membrane composed of egg-yolk lecithin, cholesterol, and diethyl phosphoric acid with a molar ratio of egg-yolk lecithin:cholesterol:diethyl phosphoric acid of 4:4:2 containing the egg-yolk lecithin at 0.9 wt % and controlled to have a negative surface charge at pH 7.0 with a ratio of 1:5 and stirred for the atelocollagen to be adsorbed by the liposome, and one of hyaluronic acid or hydrolyzed elastin.

5. A skin cosmetic containing an aqueous solution of a liposome modified with a collagen, wherein an aqueous solution containing atelocollagen at 0.5 wt % being a water-soluble collagen controlled to have a negative surface charge by alkaline treatment, while having a triple helical structure, is dropped into an aqueous solution of a liposome with a liposome membrane composed of egg-yolk lecithin, cholesterol, and phosphatidylethanolamine with a molar ratio of egg-yolk lecithin:cholesterol:phosphatidylethanolamine of 4:4:2 containing the egg-yolk lecithin at 1.2 wt % and controlled to have a positive surface charge at pH 7.0 with a ratio of 2:5 and stirred for the atelocollagen to be adsorbed by the liposome, and one of hyaluronic acid or hydrolyzed elastin.

6. The skin cosmetic according to claim 4, wherein the skin cosmetic is stored by freeze-drying.

7. The skin cosmetic according to claim 5, wherein the skin cosmetic is stored by freeze-drying.

* * * * *